United States Patent [19]
Cooper

[11] 3,956,292
[45] May 11, 1976

[54] 7-(α-FUROYLUREIDOARYL AND CYCLOHEXADIENYLACETAMIDO) CEPHALOSPORIN ANTIBIOTICS

[75] Inventor: Robin D. G. Cooper, Indianapolis, Ind.

[73] Assignee: Eli Lilly and Company, Indianapolis, Ind.

[22] Filed: Mar. 3, 1975

[21] Appl. No.: 553,061

Related U.S. Application Data

[63] Continuation-in-part of Ser. No. 456,491, April 1, 1974, abandoned.

[52] U.S. Cl. .................... 260/243 C; 260/329 AM; 260/347.3; 424/246
[51] Int. Cl.² .................................. C07D 501/24
[58] Field of Search ......................... 260/243 CN

[56] References Cited
UNITED STATES PATENTS

| | | | |
|---|---|---|---|
| 3,641,021 | 2/1972 | Ryan | 260/243 C |
| 3,673,183 | 6/1972 | Erickson | 260/243 CN |
| 3,687,949 | 8/1972 | Holdrege | 260/243 C |
| 3,741,962 | 6/1973 | Breuer | 260/243 C |
| 3,766,175 | 10/1973 | Lemieux et al. | 260/243 C |
| 3,772,286 | 11/1973 | Hoover | 260/243 C |

*Primary Examiner*—Raymond V. Rush
*Assistant Examiner*—David E. Wheeler
*Attorney, Agent, or Firm*—William B. Scanlon; Everet F. Smith

[57] ABSTRACT

New cephalosporin antibiotics of the general formula

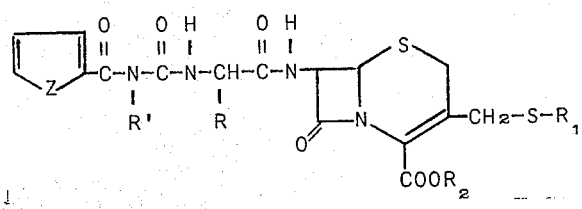

characterized by an 7-α-furoylureido or α-thenoylureido substituent and a 3-heterocyclic thiomethyl substitutent are provided. These cephalosporins and the pharmaceutically acceptable salts and certain esters, for example the acetoxymethyl esters thereof, have a broad antibiotic spectrum against both the gram-positive and gram-negative microorganisms.

16 Claims, No Drawings

7-(α-FUROYLUREIDOARYL AND CYCLOHEXADIENYLACETAMIDO) CEPHALOSPORIN ANTIBIOTICS

This application is a CIP of Ser. No. 456,491, filed Apr. 1, 1974, now abandoned.

BACKGROUND OF THE INVENTION

Several antibiotics of the cephalosporin class have achieved an important status in the treatment and control of infectious diseases of man. For example, the well known cephalosporin antibiotics, cephalothin, cephaloglycin, cephaloridine, and cephalexin have been widely used in the treatment of infections in man. Considerable effort continues to be extended in the development of new cephalosporin antibiotics with increased antibiotic activity and particularly with an expanded spectrum of activity against the gram-negative microorganisms.

DESCRIPTION OF THE PRIOR ART

Cephalosporin compounds having a substituted α-amino group in the 7-arylacetamido side chain have been previously described. For example, U.S. Pat. No. 3,646,024 describes certain 7-[α-(3-imidoylureido)arylacetamido]-cephalosporanic acids. α-Ureido phenylacetamidocephalosporanic acids have been described in British Pat. No. 1,337,000 and in U.S. Pat. No. 3,673,183.

DESCRIPTION OF THE INVENTION

This invention relates to new cephalosporin antibiotics represented by the following general formula

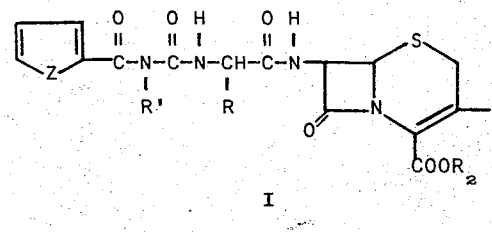

I wherein Z is O or S

R' is hydrogen or methyl;

R is phenyl, methylphenyl, mono-or dihydroxyphenyl, mono-or dihalophenyl or mono-hydroxy substituted mono-or dihalophenyl, thienyl, furyl or 1,4-cyclohexadienyl;

$R_1$ is

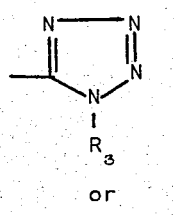

or

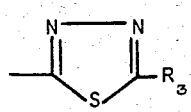

wherein $R_3$ is $C_1$–$C_4$ lower alkyl; $R_2$ is hydrogen, an indanyl group, a phthalidyl group, or an acyloxymethyl group of the formula

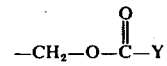

wherein Y is $C_1$–$C_4$ alkyl or phenyl; and when $R_2$ is hydrogen, the pharmaceutically acceptable salts thereof.

In the above formula I, the term "methylphenyl" refers to the mono and dimethylphenyl groups such as 4-methylphenyl, 3-methylphenyl, 3,4-dimethylphenyl, 3,5-dimethylphenyl, and the like. "Hydroxyphenyl" refers to the 3- and 4-monohydroxyphenyl groups, and to the 3,4-dihydroxy- and 2,4-dihydroxyphenyl, and the like. "Halophenyl" refers to the fluoro, chloro, and bromophenyl groups such as 4-chlorophenyl, 3-chlorophenyl, 3,4-dichlorophenyl, 4-bromophenyl, 4-fluorophenyl, and the like. "Hydroxy substituted halophenyl" refers to 3-chloro-4-hydroxyphenyl, 3,5-dichloro-4-hydroxyphenyl, 3,5-dibromo-4-hydroxyphenyl, and the like. "Thienyl" and "furyl" refer to the respective 2- and 3- isomers thereof.

As described above, the heterocyclic radical in the 3-position of the cephem ring is substituted with a $C_1$–$C_4$ lower alkyl group. Representative of these groups are the 1-methyl-1H-tetrazole-5-yl group, the 1-ethyl-1H-tetrazole-5-yl group, the 5-methyl-1,3,4-thiadiazol-2-yl group, the 5-isopropyl-1,3,4-thiadiazol-5-yl group, and like lower alkyl substituted tetrazole and thiadiazole groups.

The compounds of the invention wherein R' is hydrogen are prepared by reacting a 7-phenylglycylamido, a substituted phenylglycylamido or a 1,4-cyclohexadienylglycylamido 3-tetrazolethiomethyl or thiadiazolethiomethyl substituted cephalosporin of the following formula II with furoyl or thenoyl isocyanate as illustrated by the following reaction scheme:

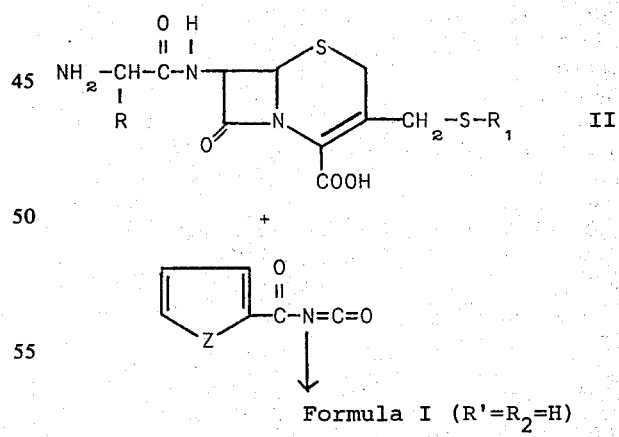

wherein R, $R_1$ and Z are as previously defined.

The compounds represented when R' is methyl are prepared by acylating the compound of the formula II with N-(α-furoyl)-N-methylcarbamoyl chloride or N-(α-thenoyl)-N-methylcarbamoyl chloride represented by the formula

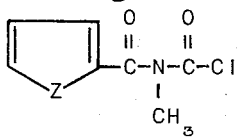

The carbamoyl chloride is prepared by reacting N-methyl-2-furamide or N-methylthiophene-2-carboxamide with n-butyllithium at −78°C. to generate the lithium salt followed by the reaction of the lithium salt with phosgene. The reaction is carried out in the cold (−78°C.) in an inert solvent such as tetrahydrofuran.

The acylation of the glycylamido cephalosporin of formula II with the carbamoyl chloride is carried out in an inert solvent at a temperature between about −15° and 10°C. in the presence of a hydrogen halide acceptor.

Inert solvents such as acetonitrile and tetrahydrofuran can be used conveniently. Hydrogen halide acceptors such as the tertiary amines, triethylamine, and pyridine; and the alkylene oxides such as propylene oxide and butylene oxide can be used. Equimolar amounts of the starting material and the N-(α-furoyl)-N-methylcarbamoyl chloride are used. In an example of the preparation of a compound of formula I wherein R' is methyl, 7-(D-phenylglycylamido)-3-(1-methyl-1H-tetrazole-5-ylthiomethyl)-3-cephem-4-carboxylic acid is suspended in dry tetrahydrofuran and solubilized by adding bis-(trimethylsilyl)-acetamide to the suspension. The solution is cooled to about 0°C. and an equimolar amount of N-(α-furoyl)-N-methylcarbamoyl chloride in tetrahydrofuran is added. The mixture is stirred in the cold for about 2 hours, is allowed to warm to room temperature, and the product extracted with an organic solvent such as ethyl acetate.

The 7-thienylglycylamido, 7-furylglycylamido, 7-phenylglycylamido and 7-substituted phenylglycylamido-3-heterocyclic thiomethyl cephalosporin starting materials of the formula II are prepared according to the procedures described by Ryan in U.S. Pat. No. 3,641,021. According to the described procedure, a 7-amino-3-heterocyclic-thiomethyl-substituted cephalosporin nucleus compound is acylated with an active derivative of phenylglycine or a substituted phenylglycine, for example, the acid chloride in the presence of a hydrogen halide acceptor such as triethylamine or sodium carbonate, to provide the acylated phenylglycylamido cephalosporin starting material.

The compounds of the formula II wherein R is the 1,4-cyclohexadienyl-1-yl group are prepared by acylation of the 7-amino-3-(1-lower alkyl-1H-tetrazole-5-ylthiomethyl) or (5-lower alkyl-1,3,4-thiadiazole-2-ylthiomethyl)-3-cephem-4-carboxylic acid with an active derivative of α-amino-α-(1,4-cyclohexadienyl) acetic acid described in U.S. Pat. No. 3,682,981. The cyclohexadienyl acetic acid is converted to an active derivative such as that formed with chloroethyl formate for use as the acylating reagent.

The reaction of the starting material of the formula II with furoyl or thenoyl isocyanate is carried out in the following manner. The starting material of the formula II is suspended in an inert solvent at about 20°–25°C. and a silylating agent such as bis-(trimethylsilyl)acetamide (BSA) or monosilylacetamide (MSA) is added in excess to form a homogeneous solution. Inert solvents such as tetrahydrofuran, dichloromethane, chloroform, or dioxane can be used. After obtaining a solution of the silylated derivative of the starting material, the reaction mixture is cooled in a dry ice-acetone bath to a temperature of approximately −75° to −80°C. To the cold solution is added, in excess, furoylisocyanate. The reaction mixture is then allowed to stir in the cold for about 3 hours and is thereafter allowed to warm to room temperature. Methanol is added to the reaction mixture to decompose excess silylating agent and the mixture is then evaporated under reduced pressure to remove the volatile solvents. The ureido reaction product is then extracted from the residue with ethyl acetate. The product is purified with an acid-base wash and can be further purified by recrystallization.

By way of illustration of the above preparative methods, 7-amino-3-(1-methyl-1H-tetrazole-5-ylthiomethyl)-3-cephem-4-carboxylic acid is acylated with phenylglycyl chloride hydrochloride in the presence of sodium carbonate to yield 7-phenylglycylamido-3-(1-methyl-1H-tetrazole-5-ylthiomethyl)-3-cephem-4-carboxylic acid. The above acylation product is then reacted with furoylisocyanate following the solubilization of the phenylglycylamido acylation product in tetrahydrofuran with MSA, to provide a compound of the invention wherein R is phenyl, $R_1$ is the 1-methyl-1H-tetrazole substituent, R' is H and $R_2$ is hydrogen.

The compounds represented by formula I wherein $R_2$ is an acyloxymethyl group are prepared by reacting a salt, for example, an alkali metal salt of the free acid compound of formula I with a lower alkanoyloxymethyl halide or with a halomethyl benzoate. Lower alkanoyloxymethyl halides which can be employed are, for example, chloromethyl acetate, chloromethyl propionate, bromomethyl acetate, bromomethyl butyrate, chloromethyl pivaloate, and like halomethyl esters of the lower alkyl straight and branced chain $C_1$–$C_4$ alkyl carboxylic acids. When Y is phenyl, bromo or chloromethylbenzoate can be used in like manner to prepare the benzoyloxymethyl ester. The reaction is carried out by reacting the salt of a cephalosporin acid of the formula I, for example, the sodium or potassium salt with the halomethyl ester in an inert solvent from about 20° to about 55°C. Inert solvents which can be employed include, for example, dimethylformamide (DMF), dimethylacetamide (DMAC), tetrahydrofuran, and dioxane. For example, sodium 7-[α-(3-furoyl-1-ureido)phenylacetamido]-3-(1-methyl-1H-tetrazole-5-ylthiomethyl)-3-cephem-4-carboxylate is reacted in aqueous DMF with chloromethyl acetate to provide the acetoxymethyl ester of the cephalosporin acid.

The 5-indanyl esters of the formula I are prepared by esterifying the cephalosporin acid with the phenolic 5-indanol. The indanyl esters can be prepared by the conventional procedures used for preparing phenolic esters of carboxylic acids. For example, an active derivative of the cephalosporin acid such as is formed with ethylchloroformate is reacted with 5-indanol.

The phthalidyl esters of the formula I are prepared by reacting bromophthalide with a salt of the cephalosporin acid, for example, the sodium or potassium salt. Bromophthalide of the formula

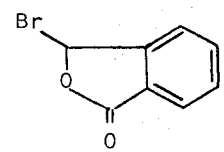

is prepared in known manner by the reaction of phthalide with N-bromosuccinimide.

The acyloxymethyl esters of the formula I are orally effective forms of the antibiotic acids.

Pharmaceutically acceptable salts of the compounds represented by formula I are prepared by methods commonly practiced in the cephalosporin art. Representative pharmaceutically acceptable salts include the alkali metal salts, for example, the sodium, potassium, and lithium salts, the calcium salt, the ammonium salt, the lower aliphatic ammonium salts, for example, those salts formed with methylamine, dimethylamine, diethylamine, di-n-propylamine, and the like; and the hydroxyalkyl ammonium salts, for example, those formed with ethanolamine or diethanolamine. Preferred pharmaceutically acceptable salts include the alkali metal salts, for example, the sodium salt and the potassium salt. The pharmaceutically acceptable salts of the compounds of formula I are prepared by methods well known in the cephalosporin art. For example, the free acid form of the antibiotic is neutralized with an alkali metal hydroxide or carbonate or with ammonium hydroxide or with the desired alkylamine or ethanolamine to form the salt.

The compounds of the present invention represented by formula I are illustrated by the following compounds.

7-[α-(3-α-furoyl-1-ureido)-α-phenylacetamido]-3-(1-methyl-1H-tetrazole-5-ylthiomethyl)-3-cephem-4-carboxylic acid, 7-[α-(3-α-furoyl-1-ureido)-α-(4-hydroxyphenyl)-acetamido]-3-(5-methyl-1,3,4-thiadiazole-2-ylthiomethyl)-3-cephem-4-carboxylic acid, 7-[α-(3-α-furoyl-1-ureido)-α-(α-thienyl)acetamido]-3-(1-ethyl-1H-tetrazole-5-ylthiomethyl)-3-cephem-4-carboxylic acid, 7-[α-(3-α-furoyl-1-ureido)-α-(α-furyl)acetamido]-3-(5-isopropyl-1,3,4-thiadiazole-2-ylthiomethyl-3-cephem-4-carboxylic acid, 7-[α-(3-α-furoyl-1-ureido)-α-(3-chloro-4-hydroxyphenyl)acetamido]-3-(1-methyl-1H-tetrazole-5-ylthiomethyl)-3-cephem-4-carboxylic acid, 7-[α-(3-α-furoyl-1-ureido)-α-(3-hydroxyphenyl)-acetamido]-3-(5-methyl-1,3,4-thiadiazole-2-ylthiomethyl)-3-cephem-4-carboxylic acid, 7-[α-(3-α-furoyl-1-ureido)-α-(1,4-cyclohexadien-1-yl)acetamido]-3-(1-methyl-1H-tetrazole-5-ylthiomethyl)-3-cephem-4-carboxylic acid, 7-[α-(3-α-furoyl-1-ureido)-α-(4-chlorophenyl)-acetamido]-3-(5-methyl-1,3,4-thiadiazole-2-ylthiomethyl)-3-cephem-4-carboxylic acid, 7-[α-(3-α-furoyl-1-ureido)-α-(4-methylphenyl)-acetamido]-3-(5-ethyl-1,3,4-thiadiazole-2-ylthiomethyl)-3-cephem-4-carboxylic acid, 7-[α-(3-α-furoyl-1-ureido)-α-(3,5-dichloro-4-hydroxyphenyl)acetamido]-3-(1-methyl-1H-tetrazole-5-ylthiomethyl)-3-cephem-4-carboxylic acid, 7-[α-(3-α-furoyl-1-ureido)-α-(3-bromophenyl)-acetamido-3-(1-methyl-1H-tetrazole-5-ylthiomethyl)-3-cephem-4-carboxylic acid, 7[α-(3-α-thenoyl)-1-ureido)-α-phenylacetamido]-3-(1-methyl-1H-tetrazole-5-ylthiomethyl)-3-cephem-4-carboxylic acid, 7-[α-(3-α-thenoyl-1-ureido)-α-(4-hydroxyphenyl)-acetamido]-3-(1-methyl-1H-tetrazole-5-ylthiomethyl)-3-cephem-4-carboxylic acid, 7-[α-(3-α-thenoyl-1-ureido)-α-(α-thienyl)acetamido]-3-(5-methyl-1,3,4-thiadiazole-2-ylthiomethyl)-3-cephem-4-carboxylic acid, 7-[α-(3-α-thenoyl-3-methyl-1-ureido)-α-phenylacetamido]-3-(1-methyl-1H-tetrazole-5-ylthiomethyl)-3-cephem-4-carboxylic acid, 7-[α-(3-β-thenoyl-1-ureido)-α-phenylacetamido]-3-(5-methyl-1,3,4-thiadiazole-2-ylthiomethyl-3-cephem-4-carboxylic acid, 7-[α-(3-α-furoyl-3-methyl-1-ureido)-α-phenylacetamido]-3-(1-methyl-1H-tetrazole-5-ylthiomethyl)-3-cephem-4-carboxylic acid, 7-[α-(3-α-furoyl-3-methyl-1-ureido)-α-(α-thienyl)-acetamido]-3-(5-methyl-1,3,4-thiadiazole-2-ylthiomethyl)-3-cephem-4-carboxylic acid, 7-[α-(3-α-furoyl-3-methyl-1-ureido)-α-(3-chloro-4-hydroxyphenyl)acetamido]-3-(1-methyl-1H-tetrazole-5-ylthiomethyl)-3-cephem-4-carboxylic acid, 7-[α-(3-α-furoyl-3-methyl-1-ureido)-α-(4-hydroxyphenyl)acetamido)-3-(5-methyl-1,3,4-thiadiazole-2-ylthiomethyl)-3-cephem-4-carboxylic acid, and the pharmaceutically acceptable non-toxic salts thereof.

The compounds of the invention represented by formula I and the pharmaceutically acceptable salts thereof inhibit the growth of microorganisms pathogenic to animals and man. In particular, these compounds inhibit the growth of a broad spectrum of gram-negative and gram-positive microorganisms. They are further active in inhibiting the growth of penicillin resistant Staphylococcus organisms. Accordingly, the compounds of the invention are useful in combating infections in animals and man attributable to gram-positive and gram-negative microorganisms. The furoyl and thenoylureidocephalosporins are effective against gram-negative microorganisms of the indole-positive and indole-negative Proteus sp., the Aerobacter sp., the Pseudomonas, the Enterobacter sp., the Serratia, e.g., S. marcescens, *Escherichia coli*, and Klebsiella. They are also highly effective against the Streptococcus D group of bacteria as well as *Staphylococcus aureus* and penicillin resistant strains of Staphylococcus.

The compounds of the invention can be administered by the parenteral route, for example, intramuscularly or intravenously. When administered in non-toxic doses ranging between about 25 and about 1,000 mg. per kg. of the patient's body weight, the compounds are effective in the treatment of infectious diseases attributable to both the gram-positive and gram-negative microorganisms. The compounds of this invention can be formulated for such administrative routes as aqueous suspensions or solutions suitable for injection. For example, the compounds of the invention, as the alkali metal salts, can be employed in sterile aqueous solutions for injection or they can be prepared as sterile suspensions in an inert pharmaceutical carried suitable for injection. When administered intravenously, the salt form of the compound of the invention, for example, the sodium salt, can be dissolved in one of the standard clinical I.V. solutions, for example, I.V. dextrose, for administration via I.V. drip.

Preferred compounds of the present invention are those represented by formula I wherein R is phenyl, hydroxyphenyl, halophenyl, hydroxy substituted halophenyl, or thienyl.

An especially preferred group of compounds of this invention are those represented when R is phenyl, hydroxyphenyl, or hydroxy substituted halophenyl especially hydroxy substituted chlorophenyl, and the pharmaceutically acceptable non-toxic salts thereof. The preferred compounds described above are illustrated by:

7-[α-(3-α-furoyl-1-ureido)-α-phenylacetamido]-3-(1-methyl-1H-tetrazole-5-ylthiomethyl)-3-cephem-4-carboxylic acid, 7-[α-(3-α-furoyl-1-ureido)-α-(4-hydroxyphenyl)-acetamido]-3-(5-methyl-1,3,4-thiadiazole-2-ylthiomethyl)-3-cephem-4-carboxylic acid, 7-[α-(3-α-furoyl-1-ureido)-α-(3-hydroxyphenyl)-acetamido]-3-(1-methyl-1H-tetrazole-5ylthiomethyl)-3-cephem-4-carboxylic acid, 7-[α-(3-α-furoyl-1-ureido)-α-(3-chloro-4hydroxyphenyl)acetamido]-3-(1-methyl-1H-tetrazole-5-ylthiomethyl)-3-cephem-4-carboxylic acid, 7-[α-(3-α-furoyl-1-ureido0-α-(3,5-dichloro-4-hydroxyphenyl)acetamido]-3-(5-methyl-1,3,4-thiadiazole-2-ylthiomethyl)-3-cephem-4-carboxylic acid, 7-[α-(3-α-furoyl-3-methyl-1ureido)-α-(4-hydroxyphenyl)acetamido]-3-(1-methyl-1H-tetrazole-5-ylthiomethyl)-3-cephem-4-carboxylic acid, and the pharmaceutically acceptable non-toxic salts thereof.

The antibiotic activity of the compounds of the invention is illustrated by the in vitro data presented in the following Tables I and II for two of the preferred compounds. In the tables, the minimum inhibitory concentrations (MIC) of the test compounds versus the indicated gram-positive and gram-negative microorganisms is presented. The MIC values were determined by the gradient plate method which is essentially the method described by Bryson and Szybalski, Science, 116, 45-46 (1952).

Table I lists the in vitro antibiotic activity demonstrated by the test compounds against representative gram-negative microorganisms. Table II lists the inhibitory activity in terms of MIC values against clinical isolates of penicillin resistant Staphylococcus microorganisms both in the presence of and in the absence of serum.

TABLE I

Antibiotic Activity of 7-[α-(3-Furoyl-1-ureido)phenyl-(hydroxyphenyl)acetamido]cephalosporins vs. Grams⁻ Microorganisms

| Test Organism | MIC (mcg/ml) Test Compound | |
|---|---|---|
| | A[1] | B[2] |
| *Shigella sp.* | 5.5 | 5.5 |
| *Escherichia coli* | 7.0 | 5.8 |
| *Klebsiella pneumoniae* | 5.0 | 6.3 |
| *Aerobacter aerogenes* | 7.5 | 6.5 |
| *Salmonella heidelberg* | 6.8 | 5.8 |
| *Pseudomonas aeruginosa* | 12.3 | 10.7 |
| *Serratia marcescens* | 19.5 | 14.5 |

[1]Test Compound A=7-[α-(3-α-furoyl-1-ureido)-α-phenylacetamido]-3-(1-methyl-1H-tetrazole-5-ylthiomethyl)-3-cephem-4-carboxylic acid.
[2]Test Compound B=7-[α-(3-α-furoyl-1-ureido)-α-(4-hydroxyphenyl)acetamido]-3-(1-methyl-1H-tetrazole-5-ylthiomethyl)-3-cephem-4-carboxylic acid.

TABLE II

Antibiotic Activity of 7-[α-(3-Furoyl-1-ureido)-phenyl(hydroxyphenyl)acetamidocephalosporins vs. Resistant Staphylococcus

| Resistant Staph. | MIC (mcg/ml) Test Compound | | | |
|---|---|---|---|---|
| | A | | B | |
| | NS[2] | S[3] | NS | S |
| V-41 | 3.0 | 8.0 | 5.0 | >20 |
| V-32 | 4.5 | 8.0 | 13.7 | >20 |
| X-400 | >20 | >20 | >20 | >20 |
| V-84 | 0.4 | 1.0 | 1.0 | 1.0 |
| X1.1 | 0.4 | 1.0 | 1.0 | 1.0 |

[1]Test compounds A & B are respectively the test compounds of Table I.
[2]Compound tested in the absence of serum.
[3]Compound tested in the presence of serum.

As indicated by the in vitro data presented above for two of the preferred compounds of this invention, the furoylureido cephalosporin compounds disclosed herein are resistant to the action of the enzymes, penicillinase and cephalosporinase, generated respectively by the penicillin-resistant Staphylococci and the gram-negative organisms.

The preparation of the compounds of the invention as represented by formula I is further illustrated by the following examples.

EXAMPLE 1

To a suspension of 0.6693 g. of 7-phenylglycylamido-3-(1-methyl-1H-tetrazole-5-ylthiomethyl)-3-cephem-4-carboxylic acid in 100 ml. of dry tetrahydrofuran was added an excess of monosilyl acetamide to form a solution. Linde 4A molecular sieve was added and the mixture was cooled in dry ice-acetone bath. An excess of furoyl isocyanate was added to the cold mixture with stirring. Stirring was continued in the cold for 2 hours and then the mixture was allowed to warm to room temperature. Fifty milliliters of methanol were added and the reaction mixture was filtered. The filtrate was evaporated under reduced pressure to remove volatile solvents. The residue was dissolved in aqueous sodium bicarbonate and the solution was extracted with ethyl acetate. The aqueous phase was acidified to about pH 1.5–2.0 with dilute hydrochloric acid and was extracted with ethyl acetate. The extract was concentrated and was then diluted with about an equal volume of petroleum ether to precipitate the product, 7-[α-(3-α-furoyl-1-ureido)-α-phenylacetamido]-3-(1-methyl-1H-tetrazole-5-ylthiomethyl)-3-cephem-4 -carboxylic acid.

The nuclear magnetic resonance spectrum of the product run in deuterated dimethyl sulfoxide was in agreement showing peaks at δ5.10 and δ5.70 for the $C_6$ and $C_7$ β-lactam protons; multiplets at δ4.32 and δ3.65 for the methylene protons and a singlet at δ4.00 for the N-methyl protons of the tetrazole group.

EXAMPLE 2

To a suspension of 0.955 g. of 7-(4-hydroxyphenylglycylamido)-3-(1-methyl-1H-tetrazole-5-ylthiomethyl)-3-cephem-4-carboxylic acid in 100 ml. of tetrahydrofuran was added excess monosilylacetamide. To the resultant solution was added molecular sieve (Linde 4A molecular sieve) and the mixture cooled in a dry-ice acetone bath. A slight excess of furoyl isocyanate was then added with stirring. The reaction mixture was stirred in the cold for 3 hours and was then allowed to warm to room temperature. Methanol, 100 ml., was added and the mixture was then evaporated under reduced pressure to remove volatile solvents. The residue was dissolved in an aqueous solution of sodium bicarbonate and the solution was washed with ethyl acetate. The solution was then acidified with dilute hydrochloric acid to about pH 2 and extracted with ethyl acetate. The extract was concentrated and the concentrate diluted with petroleum ether to precipitate the reaction product, 7-[α-(3-furoyl-1-ureido)-4-hydroxyphenylacetamido]-3-(1-methyl-1H-tetrazole-5-ylthiomethyl)-3-cephem-4-carboxylic acid. The product was further purified by crystallization from methanol-diethyl ether-pentane (Skelly-solve-B).

EXAMPLE 3

Following the procedures of Example 1, furoyl isocyanate is reacted with 7-phenylglycylamido-3-(5-methyl-1,3,4-thiadiazole-2-ylthiomethyl)-3-cephem-4-carboxylic acid to obtain 7-[α-(3-α-furoyl-1-ureido)-α-phenylacetamido]-3-(5-methyl-1,3,4-thiadiazole-2-ylthiomethyl)-3-cephem-4-carboxylic acid.

EXAMPLE 4

7-[α-(3-α-Furoyl-1-ureido)-α-(3-chloro-4-hydroxyphenyl)acetamido]-3-(1-methyl-1H-tetrazole-5-ylthiomethyl)-3-cephem-4-carboxylic acid is prepared by the reaction of furoyl isocyanate with 7-(3-chloro-4-hydroxyphenylglycylamido)-3-(1-methyl-1H-tetrazole-5-ylthiomethyl)-3-cephem-4-carboxylic acid.

EXAMPLE 5

To a suspension of 461 mg 7-phenylglycylamido-3-(1-methyl-1H-tetrazole-5-ylthiomethyl)-3-cephem-4-carboxylic acid in 8 ml. of dry acetonitrile containing 2 ml. of propylene oxide was added with stirring 1 ml. of bis-(trimethylsilyl)acetamide (BSA). The resulting orange solution was cooled to 0°C. and a solution of a slight molar excess of N-(2-furoyl)-N-methylcarbamoyl chloride in 2 ml. of dry acetonitrile was added. The reaction mixture was stirred for 2 hours in the cold and was then allowed to warm to room temperature.

The reaction mixture was filtered and the methanol was added to the filtrate to destroy any excess BSA present. The filtrate was evaporated and the residue was dissolved in a mixture of ethyl acetate and water. The pH of the mixture was adjusted to 2 and the organic layer separated. The organic layer was washed with water, dried, and evaporated to yield the reaction product, 7-[α-(3-α-furoyl-3-methyl-1-ureido)-α-phenylacetamido]-3-(1-methyl-1H-tetrazole-5-ylthiomethyl)-3-cephem-4-carboxylic acid. The product was crystallized from acetone-ether to yield 156 mg. of purified product.

EXAMPLE 6

To a solution of 511 mg. of 7-(3-chloro-4-hydroxyphenylglycylamido)-3-(1-methyl-1H-tetrazole-5-ylthiomethyl)-3-cephem-4-carboxylic acid in 1 ml. of tetrahydrofuran and 1 ml. of bis-(trimethylsilyl)acetamide was added a solution of 2 ml. of propylene oxide in 8 ml. of acetonitrile. The resulting solution was cooled to 0°C. and a solution of 2 ml. of N-(2-furoyl)-N-methylcarbamoyl chloride in 2 ml. of acetonitrile was added. The dark reaction mixture was stirred at 0°C. for 2 hours and was then allowed to warm to room temperature. The mixture was filtered and 3 ml. of methanol were added to the filtrate to destroy any excess silyl reagent. The filtrate was evaporated and the residue dissolved in a mixture of ethyl acetate and water. With stirring the pH of the mixture was adjusted to 2 with dilute hydrochloric acid. The organic phase was separated and was washed with water, dried, and evaporated under reduced pressure. The reaction product residue, 7-[α-(3-furoyl-3-methyl-1-ureido)-α-(3-chloro-4-hydroxyphenyl)acetamido]-3-(1-methyl-1H-tetrazole-5-ylthiomethyl)-3-cephem-4-carboxylic acid was crystallized from a mixture of ethyl acetate-diethyl ether-petroleum ether to yield 74 mg. of crystalline product.

EXAMPLE 7

7-[α-(3-α-furoyl-1-ureido)-α-(α-thienyl)acetamido]-3-(1-methyl-1H-tetrazole-5-ylthiomethyl)-3-cephem-4-carboxylic acid.

To a suspension of 467 mg of 7-[α-(α-thienyl)-α-aminoacetamido]-3-(1-methyl-1H-tetrazole-5-ylthiomethyl)-3-cephem-4-carboxylic acid in 100 ml of dry THF were added 2 g of mono-(trimethylsilyl)acetamide (MSA). When solution had occurred a small amount of molecular sieve was added to maintain dryness and the solution was cooled to 0°C. To the cold solution was added a solution of an excess of furoyl isocyanate in 2 ml of THF. The reaction mixture was stirred at 0°C. for 3 hours and was then allowed to warm to room temperature. The reaction mixture was filtered and 5 ml of methanol were added to the filtrate. The filtrate was evaporated and the residue was layered with ethyl acetate and water. The pH of the aqueous phase was adjusted to 2 with dilute hydrochloric acid and the organic layer was separated. The organic layer was treated with a dilute solution of sodium bicarbonate to pH 7.2. The aqueous layer was separated and acidified to pH 2 with dilute hydrochloric acid at ice bath temperature. The acidified solution was extracted with ethyl acetate. The extract was dried and evaporated and the residue recrystallized from a mixture of acetone-diethyl ether-petroleum ether to yield a first crop of product weighing 45 mg, a second crop weighing 83 mg and an additional 24 mg of product from the filtrate.

EXAMPLE 8

7-[α-(3-α-furoyl-3-methyl-1-ureido)-α-(1,4-cyclohexadienyl)-acetamido]-3-(1-methyl-1H-tetrazole-5-ylthiomethyl)-3-cephem-4-carboxylic acid.

By following the procedures described in Example 5, 463 mg of impure 7-[α-(1,4-cyclohexadienyl)-α-amino-acetamido]-3-(1-methyl-1H-tetrazole-5-ylthiomethyl)-3-cephem-4-carboxylic acid was dissolved in 15 ml of methylene chloride containing excess bis-(trimethylsilyl)acetamido (BSA), propylene oxide was added to the solution followed by a slight molar excess of N-(2-furoyl)-N-methylcarbamoyl chloride. After stirring for 2 hours in the cold 74 mg of the product was recovered as an amorphous powder.

EXAMPLE 9

7-[α-(3-α-thenoyl-1-ureido)-α-(α-thienyl)acetamido]-3-(1-methyl-1H-tetrazole-5-ylthiomethyl)-3-cephem-4-carboxylic acid.

To a solution of 467 mg of 7-(α-amino-α-thienylacetamido)-3-(1-methyl-1H-tetrazole-5-ylthiomethyl)-3-cephem-4-carboxylic acid in 100 ml of dry THF, formed by the addition of 1 ml of BSA, was added at 0°C. a solution containing a molar excess of α-thienylisocyanate in 2 ml of dry THF. The reaction mixture was stirred for 3 hours at 0°C. and was then allowed to warm to room temperature. The product was recovered from the reaction mixture by following the isolation procedures described in Example 7. The product was recrystallized from a mixture of acetone-diethyl ether-petroleum ether to yield 156 mg.

EXAMPLE 10

7-[α-(3-α-furoyl-3-methyl-1-ureido)-α-(α-thienyl)acetamido]-3-(1-methyl-1H-tetrazole-5-ylthiomethyl)-3-cephem-4-carboxylic acid.

A suspension of 234 mg of 7-[(α-amino-α-(α-thienyl)-acetamido]-3-(1-methyl-1H-tetrazole-5-ylthiomethyl)-3-cephem-4-carboxylic acid in 50 ml of dry acetonitrile was solubilized with 5 ml of BSA and the slightly orange solution was cooled to 0°C. To the cold solution were added 2 ml. of propylene oxide and a stoichiometric excess of N-(α-furoyl)-N-methylcarbamoyl chloride. The reaction mixture was stirred 2 hours at 0°C., one hour at room temperature and methanol was added to decompose the silylating agent. The mixture was evaporated and the residue extracted with ethyl acetate at pH2. The extract was washed with water, dried and evaporated under vacuum. The dried residue was recrystallized from a mixture of acetone-diethylether-petroleum ether to yield 141 mg of the product.

I claim:

1. The compound of the formula

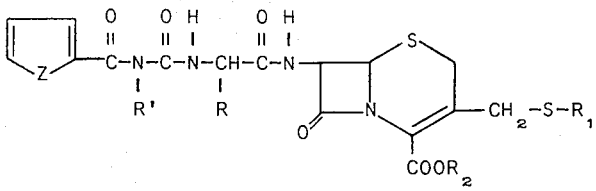

wherein Z is O or S;

R' is hydrogen or methyl;

R is phenyl, methylphenyl, mono- or dihydroxyphenyl, mono- or dihalophenyl, monohydroxy substituted mono or dihalophenyl, thienyl, furyl, or 1,4-cyclohexadienyl;

$R_1$ is

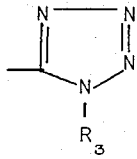 or 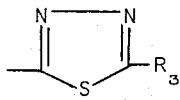

wherein $R_3$ is $C_1$–$C_4$ alkyl;

$R_2$ is hydrogen, indanyl, phthalidyl, or an acyloxymethyl group of the formula

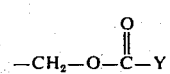

wherein Y is $C_1$–$C_4$ alkyl or phenyl;

and when $R_2$ is hydrogen, the pharmaceutically acceptable nontoxic salts thereof.

2. The compound of claim 1, wherein R is phenyl, mono- or dihydroxyphenyl, mono- or dihalophenyl, monohydroxy substituted mono-or dihalophenyl, or thienyl.

3. The compound of claim 2, wherein R is phenyl, monohydroxyphenyl, or monohydroxy substituted mono- or dihalophenyl, and $R_2$ is hydrogen.

4. The compound of claim 3, wherein $R_1$ is

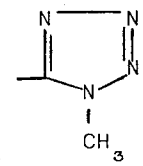

5. The compound of claim 4, said compound being 7-[α-(3-α-furoyl-1-ureido)-α-phenylacetamido]-3-(1-methyl-1H-tetrazole-5-ylthiomethyl)-3-cephem-4-carboxylic acid.

6. The compound of claim 4, said compound being 7-[α-(3-α-furoyl-1-ureido)-α-(4-hydroxyphenyl)acetamido]-3-(1-methyl-1H-tetrazole-5-ylthiomethyl)-3-cephem-4-carboxylic acid.

7. The compound of claim 4, said compound being 7-[α-(3-α-furoyl-1-ureido)-α-(3-chloro-4-hydroxyphenyl)-acetamido]-3-(1-methyl-1H-tetrazole-5-ylthiomethyl)-3-cephem-4-carboxylic acid.

8. The compound of claim 4, said compound being 7-α-(3-α-furoyl-3-methyl-1-ureido)-α-(3-chloro-4-hydroxyphenyl)-acetamido]-3-(1-methyl-1H-tetrazole-5-ylthiomethyl)-3-cephem-4-carboxylic acid.

9. The compound of claim 4, said compound being 7-[α-(3-α-furoyl-3-methyl-1-ureido)-α-phenylacetamido]-3-(1-methyl-1H-tetrazole-5-ylthiomethyl)-3-cephem-4-carboxylic acid.

10. The compound of claim 3, wherein $R_1$ is

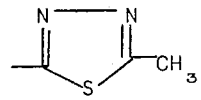

11. The compound of claim 10, wherein R' is hydrogen and R is phenyl.

12. The compound of claim 10, wherein R' is methyl and R is phenyl.

13. The compound of claim 1 wherein R is thienyl.

14. The compound of claim 13 said compound being 7-[α-(3-α-furoyl-1-ureido)-α-(α-thienyl)acetamido]-3-(1-methyl-1H-tetrazole-5-ylthiomethyl)-3-cephem-4-carboxylic acid.

15. The compound of claim 13 said compound being 7-[α-(3-α-thenoyl-1-ureido)-α-(α-thienyl)acetamido]-3-(1-methyl-1H-tetrazole-5-ylthiomethyl)-3-cephem-4-carboxylic acid.

16. The compound of claim 13 said compound being 7-[α-(3-α-furoyl-3-methyl-1-ureido)-α-(α-thienyl)acetamido]-3-(1-methyl-1H-tetrazole-5-ylthiomethyl)-3-cephem-4-carboxylic acid.

* * * * *

UNITED STATES PATENT AND TRADEMARK OFFICE
CERTIFICATE OF CORRECTION

PATENT NO. : 3,956,292
DATED : May 11, 1976
INVENTOR(S) : Robin D. G. Cooper

It is certified that error appears in the above-identified patent and that said Letters Patent are hereby corrected as shown below:

The title should read as follows: -- 7$\alpha$-FUROYL(THENOYL)-UREIDOARYL CEPHALOSPORIN ANTIBIOTICS --.

In column 1, lines 1-4, the title should read as follows: -- 7$\alpha$-FUROYL(THENOYL)UREIDOARYL CEPHALOSPORIN ANTIBIOTICS --.

In column 5, line 63, "7$\alpha$-" should read -- 7-$\alpha$- --.

In column 6, line 1, "($\alpha$-thienyl-" should read -- ($\alpha$-thienyl)- --.

In column 6, line 2, ")acetamido" should read --acetamido) --.

In column 6, lines 36-39, "Proteus", "Aerobacter", "Pseudomonas", "Enterobacter", "Serratia","S. marcescens", and "Klebsiella" should be typed in italics.

In column 6, line 42, "Staphylococcus" should be typed in italics.

In column 7, line 17, "1-ureidoO-" should read -- 1-ureido)- --.

In column 7, line 21, "1ureido" should read -- 1-ureido --.

In column 7, line 45, in Table I, "vs. Grams⁻ Microorganisms" should read -- vs. Gram⁻ Microorganisms --.

In column 10, line 2, "7-$\alpha$-(   3-furoyl" should read -- 7-$\alpha$-(3-$\alpha$-furoyl --.

In column 10, line 56, "($\alpha$-thienyl-" should read -- ($\alpha$-thienyl)- --.

UNITED STATES PATENT AND TRADEMARK OFFICE
CERTIFICATE OF CORRECTION

PATENT NO. : 3,956,292

DATED : May 11, 1976

INVENTOR(S) : Robin D. G. Cooper

It is certified that error appears in the above-identified patent and that said Letters Patent are hereby corrected as shown below:

In column 10, line 57, ")acetamido" should read -- acetamido --.

In column 11, line 5, "($\alpha$-thienyl-" should read -- ($\alpha$-thienyl)- --.

In column 11, line 6, ")acetamido" should read -- acetamido --.

In column 11, lines 39-42, in claim 1, should read as follows: -- R is phenyl, mono- or dihydroxyphenyl, mono- or dihalophenyl, monohydroxy substituted mono or dihalophenyl, or thienyl; --.

Signed and Sealed this

Tenth Day of July 1979

[SEAL]

Attest:

LUTRELLE F. PARKER

Attesting Officer

Acting Commissioner of Patents and Trademarks